United States Patent [19]

Peterson et al.

[11] Patent Number: 6,004,584

[45] Date of Patent: Dec. 21, 1999

[54] HIGHLY ABSORBENT BODY POWDERS

[75] Inventors: Liezl Gonzales Peterson, Loveland, Ohio; Patricia Alison LaFleur, Shrewsbury, Pa.; George Endel Deckner, Cincinnati, Ohio

[73] Assignee: The Procter & Gamble Company, Cincinnati, Ohio

[21] Appl. No.: 09/033,320

[22] Filed: Mar. 2, 1998

[51] Int. Cl.$^6$ .................................................. A61K 9/14
[52] U.S. Cl. ............................ 424/489; 424/69; 424/63; 424/70.1
[58] Field of Search ................................ 424/489, 69, 63, 424/70.1

[56] References Cited

U.S. PATENT DOCUMENTS

| | | | |
|---|---|---|---|
| 3,081,223 | 3/1963 | Gunning et al. | 167/39 |
| 4,014,995 | 3/1977 | Juliano et al. | 424/168 |
| 4,078,051 | 3/1978 | Pomot et al. | 424/35 |
| 4,407,789 | 10/1983 | Eigen et al. | 424/69 |
| 4,650,670 | 3/1987 | Calingham et al. | 424/65 |
| 4,659,564 | 4/1987 | Cox et al. | 424/65 |
| 4,664,910 | 5/1987 | Caserio et al. | 424/70 |
| 4,743,440 | 5/1988 | Callingham et al. | 424/46 |
| 4,837,011 | 6/1989 | Macchio et al. | 424/69 |
| 5,122,418 | 6/1992 | Nakane et al. | 424/401 |
| 5,206,012 | 4/1993 | Farer et al. | 424/69 |
| 5,525,331 | 6/1996 | Betts | 424/65 |

FOREIGN PATENT DOCUMENTS

| | | | |
|---|---|---|---|
| 0701812 A1 | 3/1996 | European Pat. Off. | A61K 7/32 |
| 27 31 520 A1 | 1/1979 | Germany | A61K 7/32 |
| 229304 A1 | 11/1985 | Germany | A61K 7/035 |
| 53-41440 | 4/1978 | Japan | A61K 7/32 |
| 7-100644 | 11/1995 | Japan | A61K 7/00 |

OTHER PUBLICATIONS

"Skin Products for Babies", Harry's Cosmeticology, (1982), pp. 112–113, 288–297, 300–304, 757–761, 764–765.
"Toiletries and Cosmetics Compositions", Research Disclosure, (1994), pp. 259–260.
Vivid Body Talc, Liz Claiborne.
Shower to Shower Absorbent Body Powder, Johnson & Johnson.
Vagisil Feminine Powder, Dist. by COMBE Incorporated.
Johnson's Baby Powder, Johnson & Johnson.
Johnson's Baby Baby Powder, Johnson & Johnson.
Baby Magic, Dist. by The Mennen Co.
Medicated Bismoline Powder.
Aloe vera Deodorant Foot Talc, Dist. by Crabtree & Evelyn.
Norforms Medicated Feminine Powder, Marketed by Personal Laboratories.
Summer's Eve Feminine Powder, Marketed by Personal Laboratories.
Yeast–X Medicated Feminine Powder, Marketed by Personal Laboratories.
Airspun Face Powder, Coty Inc.
Cover Girl Fresh Complexion Oil Control Loose Powder, Procter & Gamble, Inc.
Cover Girl Professional Translucent Loose Powder, Procter & Gamble, Inc.
Gold Bond Medicated Body Powder, Distributed by Martin Himmel Inc.
"Baby Powder", Harry's Cosmeticology (1973), pp. 543–545.
U.S. application No. 08/736,838, Peterson et al., filed Oct. 28, 1996.
U.S. application No. 08/739,091, Peterson et al., filed Oct. 28, 1996.
U.S. application No. 08/871,790, Peterson et al., filed Jun. 9, 1997.
U.S. application No. 08/871,856, Peterson et al., filed Jun. 9, 1997.
U.S. application No. 08/871,861, Peterson et al., filed Jun. 9, 1997.
U.S. application No. 08/871,092, Peterson et al., Jun. 9, 1997.

*Primary Examiner*—Thurman K. Page
*Assistant Examiner*—William E. Benston
*Attorney, Agent, or Firm*—Kirsten S. Stone; James C. Kellerman

[57] ABSTRACT

The present invention relates to moisture absorbing body powder compositions. Through careful formulation of the powder carrier, the present invention also provides moisture absorbing body powders with surprisingly good skin feel characteristics. The powder carrier which provides the good skin feel characteristics comprises skin feel components selected from the group consisting of: starch, metallic stearates, fatty acid derivatives, nylon, polyethylene, polytetrafluoroethylene, and platelet-shaped powders.

12 Claims, No Drawings

HIGHLY ABSORBENT BODY POWDERS

BACKGROUND OF THE INVENTION

Human skin secretes substances such as eccrine and apocrine sweat, and lipid-soluble sebum. Such skin secretions can be uncomfortable and even unhealthy. Skin secretions provide food and a moist environment for microbes to proliferate, which may result in embarrassing body odor and even fungal or bacterial skin infections. Additionally, moisture from skin secretions can result in skin rashes and other uncomfortable skin related disorders. These problems are magnified in occluded skin areas and at intertriginous skin sites where skin to skin contact and moisture build-up are frequent. Furthermore, other forms of natural body moisture such as urine, menses, or vaginal discharge can compound these problems, particularly in the pelvic region.

Attempts have been made to combat these problems by minimizing moisture on the skin through the use of antiperspirants, which may be harsh. Additionally, antiperspirants prevent perspiration which may be unhealthy when applied to the entire body. Other attempts to minimize moisture involve the application of body powders. However, body powders of the prior art provide minimal control of excess moisture. Thus, there remains a need for a body powder capable of providing enhanced control of excess moisture on the skin.

It has been discovered that body powders containing silicas, silicates, and carbonates provide the desired moisture absorption lacking in prior art powders. Surprisingly, it has also been discovered that body powders having high absorptive characteristics can be formulated to provide powders having good slip/lubricity characteristics and which do not cause over-drying of the skin. These and other objects of the present invention will become readily apparent from the detailed description which follows.

All percentages, ratios, and parts herein, in the Specification, Examples, and claims are by weight unless otherwise stated. The term "g", as used herein, means gram.

SUMMARY OF THE INVENTION

The present invention relates to moisture absorbing body powders. The present invention also relates to moisture absorbing powders which have good skin feel characteristics.

DETAILED DESCRIPTION OF THE INVENTION

The present invention relates to moisture absorbing body powder compositions. Through careful formulation of the powder carrier, the present invention also provides moisture absorbing body powders with surprisingly good skin feel characteristics.

The composition of the present invention comprises dry ingredients preferably having particle sizes of from about 1 micron to about 100 microns; more preferred from about 1 micron to about 60 microns; and most preferred from about 1 micron to about 30 microns. As used herein, the particle size refers to the largest dimension of the particle and to the ultimate (or primary) particles.

The term "occluded skin", as used herein, refers to regions of a human body covered by undergarments, such as the pelvic area, panty-area, and bra-line; and skin-folds or intertriginous regions, where there is continuing skin-to-skin contact.

The term "body fluids", as used herein, means eccrine sweat, apocrine sweat, build up of sensible moisture from transepidermal water loss, vaginal discharge, urine, and mixtures thereof. The phrase "excess moisture", as used herein, means an undesirable and/or unhealthy level of body fluids deposited on human skin. Where undesirable body fluids are from a particular source, the phrase "excess moisture" will be modified to specify those specific body fluids. For instance, the phrase "excess moisture in the form of eccrine sweat", as used herein, refers to an undesirable and/or unhealthy level of eccrine sweat deposited on human skin.

The term "moisture absorbing", as used herein, means having the capability of absorbing excess moisture from skin. Typically, the amount of moisture absorbed by the powders is referred to in grams of excess moisture per gram of powder ("g/g").

The term "skin feel characteristics", as used herein, means slip, lubricity, coated, and over-drying characteristics. The term "slip", as used herein, refers to the reduction of friction and the characteristic of smooth feeling on the skin. The term "lubricity", as used herein refers to a greasy, unctuous feeling. The term "coated", as used herein, refers to the feeling of remaining residue on skin. The term "over-drying", as used herein, refers to a negative feeling of too much drying of the skin. The term "good skin feel characteristics", as used herein, refers to a combination of maximized slip and/or lubricity characteristics and minimized coated and/or over-drying characteristics.

The term "body odor", as used herein, means odors which are generated as a result of the natural functioning of a human body. Such odors include, but are not limited to, odors produced by microorganisms of the human skin (i.e., bacterial decomposition of skin secretions), urine, or vaginal discharge, and mixtures thereof.

The term "pharmaceutically-acceptable", as used herein, means a powder suitable for topical use on the skin without undue toxicity, irritation, allergic response, and the like.

A detailed description of essential and optional components of the present invention is given below.

MOISTURE ABSORBERS:

Powders of the present invention comprise moisture absorbers to aid in reducing excess moisture, particularly on occluded skin. As used herein, the phrase "moisture absorbers" refers to silicas (or silicon dioxide), silicates or carbonates. The silicates and carbonates are those formed by reaction of a carbonate or silicate with the alkali (IA) metals, alkaline earth (IIA) metals, or transition metals. Preferred are moisture absorbers in the form of microspheres and/or ellipsoids.

It is preferred that the moisture absorbers of the present invention are included such that the final body powder is capable of absorbing from about 0.8 grams of excess moisture per gram of body powder (0.8 g/g), to about 6.0 grams of excess moisture per gram of body powder (6.0 g/g); more preferred from about 1.0 g/g to about 4.0 g/g; and most preferred from about 1.5 g/g to about 2.5 g/g.

Moisture absorbers useful in the present invention include calcium silicate, amorphous silicas, calcium carbonate, magnesium carbonate, or zinc carbonate, and mixtures thereof. Some specific examples of the silicates and carbonates useful in the present invention are more fully explained in Van Nostrand Reinhold's *Encyclopedia of Chemistry*, 4th Ed. pp. 155, 169, 556, and 849, (1984), which is incorporated herein by reference. Preferred are synthetic versions of the moisture absorbers, particularly in regards to silicas and silicates due to safety risks related to crystalline silica. Synthetic versions are formed by controlled chemical reactions in a manufacturing process rather than using a natural, mined version of these compounds which is then further refined. Synthetic carbonates useful in the present invention can be obtained from various suppliers such as Mallinckrodt or Whittaker, Clark, and Daniels. Examples of synthetic calcium silicates useful in the present invention are Hubersorb® 250 or Hubersorb® 600 available from J. M. Huber.

It is also preferred that the moisture absorbers comprise from about 2% to about 60%; preferred from about 6% to about 60%; more preferred from about 16% to about 55%; even more preferred from about 20% to about 50%; still more preferred from about 25% to about 45%; and most preferred from about 35% to about 40% by weight of the body powder composition.

Absorbent powders comprising mainly silicas for moisture control are preferred over those powders comprising mainly silicates and/or carbonates for moisture control. Most preferred are silicas which are in the form of microspheres and/or ellipsoids, as they have been found to contribute good skin feel characteristics in addition to efficient moisture absorption. Silica ellipsoids useful in the present invention are available from DuPont as ZELEC® Sil. Silica microspheres are available from KOBO as MSS-500, MSS 500/3, MSS-500/H, MSS-500/3N, MSS-500/N, and MSS-500/3N, from Presperse as Spheron L-1500, Spheron P-1000, Spheron P-1500, and from US Cosmetics as Silica Beads SB-300 and SB-700. Additionally, where increased flowability of the powder is desired, it is preferred that some of the silica of the present invention be fumed silica. Fumed silica is available from Cabot Corporation (Cab-O-Sil®) and from Degussa (Aerosil®).

Silicas are generally capable of absorbing more moisture per gram of powder than carbonates and silicates, so they need not be present at quite as high of levels in the final body powder. When silicas, particularly silica ellipsoids and silica microspheres, are intended to be the main means for moisture absorption, it is preferred that the silicas comprise from about 1% to about 40%; preferred from about 4% to about 40%; more preferred from about 7% to about 35%; even more preferred from about 10% to about 33%; still more preferred from about 15% to about 30%; and most preferred from about 20% to about 25% by weight of the body powder composition.

POWDER CARRIER:

The moisture absorbing body powders of the present invention comprise powder carriers. Powder carriers include but are not limited to cornstarch (topical starch), talc, rice starch, oat starch, tapioca starch, potato starch, legume starches, soy starch, turnip starch, microcrystalline cellulose (for example Avicel®), aluminum starch octenyl succinate (sold by National Starch & Chemical Co. as Dry Flo® Pure, Dry Flo® XT, Dry Flo® PC, and/or Dry Flo® AF (aluminum free grade)), kaolin, and mixtures thereof. Preferred is cornstarch. These powder carriers typically comprise from about 25% to about 99%, preferably from about 30% to about 80%, more preferably from about 35% to about 75%, and most preferably from about 40% to about 70%, by weight of the body powder. Preferably, where the powder carrier comprises talc, talc comprises less than about 50% by weight of the body powder. Where a body powder is intended for use in the panty area, preferably the powder comprises less than 5%, preferably less than 3%, most preferably, about 0% of talc, by weight of the body powder.

Skin feel Components: The powder carriers of the present invention can also be specially formulated to provide good skin feel characteristics, particularly where crystalline, granular, or abrasive ingredients, such as many odor control agents, also comprise the body powder. Specially formulated powder carriers are also important where increased levels of moisture absorbers, particularly moisture absorbers which do not have acceptable skin feel, are included in the body powders. The powder carriers of those absorbent body powders which have the good skin feel characteristics often comprise skin feel components. "Skin feel components", as used herein, refers to three groups of ingredients which are 1) stearates and/or fatty acid derivatives, 2) spherical particles, and 3) platelet-shaped particles. It is preferred that the body powders of the present invention comprise one or more of these skin feel components.

Stearates and/or fatty acid derivatives useful herein include metallic stearates such as magnesium stearate or zinc stearate, and similar fatty acid derivatives such as fatty acid esters which possess unctuous, oily characteristics. Examples of fatty acid esters useful herein include palmitates, oleates, laurates, linoleates, myristates, and butyrates. Zinc laurate, magnesium myristate, and zinc myristate are preferred. More preferred are zinc stearate and magnesium stearate. When included herein, stearates and/or fatty acids derivatives comprises from about 0% to about 40%; preferably from about 1% to about 30%; more preferably from about 3% to about 25%; and most preferably from about 5% to about 20%, by weight of the body powder.

Spherical particles useful herein include nylon, polyethylene, and polytetrafluoroethylene. Preferred is nylon. Examples of nylon include Nylon N-012 from Presperse, and nylons under the tradename Orgasol, from Lipo Chemicals. Polyethylene is available from Equistar Chemicals under the tradename Microthene. These spherical particles comprise from about 0% to about 40%; preferably from about 1% to about 30%, more preferably from about 5% to about 25%, and most preferably from about 10% to about 20%, by weight of the body powder.

Platelet-shaped particles which are useful herein include mica, talc, lauroyl lysine (available as Amihope LL from Ajinomoto), boron nitride, and barium sulfate. Preferred platelet-shaped particles are lauroyl lysine and mica (available as Silk Mica from Rona/EM Industries). Talc provides good skin feel characteristics, but due to safety concerns, particularly when the body powders of the present invention are to be used in the panty region, preferred embodiments of the present invention are essentially talc free. Platelet-shaped particles comprise from about 0% to about 50%; preferably from about 1% to about 47%; more preferably from about 5% to about 45%; even more preferably from about 10% to 40%; and most preferably from about 20% to about 30%, by weight of the body powder.

Preferably, the body powders of the present invention comprise at least one of the above skin feel components in addition to at least one starch. When a body powder comprises one or more of the skin feel components, the starches preferably comprise from about 25% to about 90%; more preferably from about 30% to about 75%; even more preferably from about 35% to about 60%; and most preferably from about 40% to about 50%, by weight of the body powder. Preferred body powders comprise the skin feel components at from about 5% to about 70%; more preferred at from about 10% to about 65%; even more preferred at from about 15% to about 60%; and most preferred at about 20% to about 55%, by weight of the body powder.

OPTIONAL INGREDIENTS

Odor Control Agents: The present invention may comprise odor control agents such as uncomplexed cyclodextrin, zeolites, carbon odor-controlling agents, sodium bicarbonates, and/or antimicrobial agents for added body odor control.

As used herein, the term "cyclodextrin" includes any of the known cyclodextrins such as unsubstituted cyclodextrins containing from six to twelve glucose units, especially alpha-cyclodextrin, beta-cyclodextrin, gamma-cyclodextrin and/or their derivatives and/or mixtures thereof. The term "uncomplexed cyclodextrin", as used herein, means that the cavities within the cyclodextrin in the composition of the present invention should remain essentially unfilled prior to application to skin in order to allow the cyclodextrin to absorb various odor molecules when the composition is applied to the skin. When included in the present invention, cyclodextrins comprise from about 0.1% to about 25%, preferably from about 1% to about 20%, more preferably from about 2% to about 15%, most preferably from about 3% to about 10%, by weight of the composition.

A more complete description of cyclodextrins, cyclodextrin derivatives, and cyclodextrin particle sizes useful in the present invention, and their use in body powders is described in U.S. patent application Ser. No. 08/736,838, Peterson et al., filed on Oct. 28, 1996; and in U.S. Pat. No. 5,429,628, Trinh et al., issued Jul. 4, 1995, which are both incorporated herein in their entirety by reference.

The term "zeolite", as used herein, refers to non-fibrous zeolites. When included in the present invention, zeolites may be present from about 0.1% to about 25%, preferably from about 1% to about 15%, by weight of the body powder composition. A detailed description of zeolites useful in the present invention is found in U.S. Pat. No. 5,429,628, Trinh et al., issued Jul. 4, 1995, incorporated herein in its entirety by reference.

Carbon odor-controlling agents described in U.S. Pat. No. 5,429,628 may be used in the present invention at a level of from about 0.1% to about 25%, by weight of the body powder composition.

Sodium bicarbonate is known in the art for its use as an odor absorber. An example of sodium bicarbonate and its use as an underarm deodorant is found in U.S. Pat. No. 4,382,079, to Marschner, issued May 3, 1983, which is incorporated herein in its entirety by reference. When included in the present invention, sodium bicarbonate may be present from about 0.1% to about 50%, by weight of the body powder composition.

The antimicrobial agents of the present invention are selected from a group consisting of antibacterial agents, antifungal agents, and mixtures thereof. Antimicrobial agents help destroy and/or control the amount of bacteria and/or fungi present on the skin. Preferred antimicrobial agents are zinc phenolsulfonate, zinc oxide, triclosan, Zelec® AM by DuPont, zinc ricinoleate, zinc undecylenate, and mixtures thereof. More preferred are zinc phenolsulfonate, zinc oxide, and triclosan. Triclosan is available from Ciba-Geigy as Irgasan DP-300. Examples of antimicrobial/antibacterial agents useful in the present invention are found in the *Cosmetic Bench Reference*, 1994 Edition, page 10, which is incorporated herein by reference. Examples of antifungal agents are found in the *Cosmetic Bench Reference*, 1994 Edition, page 42, which is incorporated herein by reference. When included in the present invention, these agents are at a level of from about 0.01% to about 25%. Preferably from about 0.1% to about 10%, by weight of the body powder composition.

When used on the underarms or on feet, antiperspirant ingredients may be included in the present invention. Examples of antiperspirants known in the art are found in the *Cosmetic Bench Reference*, 1994 Edition, page 13, which is incorporated herein by reference. When included in the present invention, antiperspirants may be present from about 0.1% to about 25%, by weight of the body powder composition. Preferably, however, the present powders are essentially free of anti-perspirants.

Skin Aids: The compositions of the present invention also optionally include skin aids. The term "skin aids", as used herein, refers to skin protectants, emollients, moisturizers, and antioxidants. Skin protectants useful in the present invention are found in the *Cosmetic Bench Reference*, 1994 Edition, page 53; and the Monograph on Skin Protectant Drug Products for Over-the-Counter Human Use, 21 CFR 347. Preferred skin protectants are corn starch, kaolin, mineral oil, sodium bicarbonate, dimethicone, zinc oxide, colloidal oatmeal, and mixtures thereof. When present, the skin protectants comprise from about 0.1% to about 80%, preferably from about 0.1% to about 30%, most preferably from about 0.1% to about 10%, by weight of the body powder composition.

Emollients and moisturizers useful in the present invention can be found in the *Cosmetic Bench Reference*, 1994 Edition, pages 27–32 and 46–48, incorporated herein by reference. Preferred emollients and moisturizers are tocopherol, tocopheryl acetate, aloe, vegetable oils, mineral oil, petrolatum, jojoba oil, and mixtures thereof. More preferred are encapsulated or spray/freeze dried emollients. The use of spray/freeze dried or encapsulated emollients keeps the emollients protected in the powder carrier until they are released through shearing (such as rubbing against undergarments or clothes) or through contact with skin moisture. Examples of preferred commercial spray/freeze dried aloe useful in the present invention are Terra-Dry™ Freeze Dried Aloe, Terra-Pure™ Freeze or Spray Dried Aloe, and Terra-Spray ™ Spray Dried Aloe, all from Terry Laboratories. Examples of preferred commercial encapsulated tocopheryl acetate are 3M Brand Microcapsules of Vitamin E Acetate in sunflower/mineral oil, available from 3M Encapsulated Products. When present, the emollients/moisturizers comprise from about 0.1% to about 50%, preferably from about 0.1% to about 25%, most preferably from about 0.1% to about 10%, by weight of the body powder composition.

Antioxidants useful in the present invention are found in the *Cosmetic Bench Reference*, 1994 Edition, pp. 11, 13, incorporated herein by reference. Preferred are retinol, retinyl acetate, and retinyl palmitate, and more preferred, encapsulated antioxidants. When present, the antioxidants comprise from about 0.1% to about 25%, preferably from about 0.1% to about 10%, by weight of the body powder composition.

Binders: The present invention may optionally also include dry or wet binders to help promote adhesion of the powder to the skin. Binders useful in the present invention are found in the *Cosmetic Bench Reference*, 1994 Edition, pp. 13–14, incorporated herein by reference. Preferred binders are calcium stearate, zinc stearate, magnesium stearate, isopropyl myristate, magnesium myristate, silicone, and mixtures thereof. More preferred are zinc stearate, magnesium stearate, dimethicone, and mixtures thereof. When included in the composition, the binders are at a level of from about 0.1% to about 25%, preferably from about 1% to about 15%, by weight of the body powder composition.

Flow Aids: Flow aids such as those known in the art may be included in the compositions of the present invention where increased flowability (and/or anti-caking) of the powder is desired. Examples of flow agents known in the art include tricalcium phosphate. Other flow agents are found in *McCutcheon's Functional Materials*, 1992 Edition, Vol. 2, pp. 11–12, incorporated herein by reference.

Anti-pruritics: Anti-pruritic agents such as those known in the art may be included in the compositions of the present invention. Examples of anti-pruritic agents useful in the present invention are Magnesium-L-Lactate, hydrocortisone, hydrocortisone acetate, and colloidal oatmeal. A description of anti-pruritic agents are found in the *Handbook of Non Prescription Drugs*, 10th Edition, p. 529, 1993, incorporated herein by reference. When included in the composition, anti-pruritic agents may be present from about 0.1% to about 40%, by weight of the body powder composition.

Colorants, Fragrances, and Preservatives: Colorants, dyes, fragrances, and/or preservatives can be optionally added to the compositions for visual appeal and performance impression. Colorants and preservatives suitable for use in the present invention are found in the *Cosmetic Bench Reference*, 1994 Edition, pp. 21–22; pp. 50–52, incorporated herein by reference. Fragrances known in the art may also be added to the powders herein.

PROCESS OF MAKING COMPOSITIONS

The compositions of the present invention are prepared by the following steps: creating a mixture by mixing moisture absorbers and optional ingredients in a powder carrier via a commercially available mixer such as a vee-blender, double cone blender, or ribbon blender until the mixture is uniform and creating a reduced size mixture using a commercially available size reduction technique such as hammer milling, impact milling, ball milling, or fluid energy milling until the desired particle size distribution is achieved (which may require repeating milling steps). A variety of screens may be used in the milling steps, such as those with herringbone-type perforations or round hole perforations. To achieve better homogeneity of the total mixture while blending and to minimize the creation of "fines" (undesirable, dust-like powder particles) when repeated milling steps are necessary, it is recommended that the "starting" particle size range of the ingredients in the total mixture prior to blending/milling be similar. For example, if there are present in the composition crystalline or granular materials (i.e. triclosan, cyclodextrin, or zinc phenolsulfonate) with starting particles of size greater than 100 microns while the remaining ingredients in the powder composition have starting particle sizes below 50 microns, it is suggested that the crystalline/granular materials undergo an initial milling step separate from the remaining ingredients so they can attain a size below 50 microns similar to the other ingredient' particle sizes. Thereafter, the crystalline materials of reduced size can be added to the other components of similar size and any mixing/milling steps carried out with the total mixture.

Liquid components, where included in the formula (e.g. wet binders, skin aids/protectants, or fragrances), may be incorporated into the powder by mixing them with the powder carrier, any of the powder ingredients, or the total mixture. For even dispersion of the liquid(s) onto the designated powder component(s), it is recommended that the liquid(s) be sprayed onto the powder while mixing. Further, a micronized spray will help facilitate achieving a more uniform dispersion.

METHODS OF USE

The body powders of the present invention are topically applied to human skin and/or hair, preferably to occluded skin. The powders can be delivered by placing the composition into a dispensing means and applying an effective amount via spraying, sprinkling, shaking, or rubbing the composition onto the desired skin surface. Preferably the dispensing means is a canister, a spray bottle, or a preformed wipe or a wipe of the user's own choosing, which comprises a flexible dispensing means. The term "flexible dispensing means", as used herein, includes papers, cloths, nonwovens, films, foams, sponges, rollers, pads, tissues, cotton balls, and the like. The user may also use his/her hand to apply the powders. The user may use as much or as little of the powders as he/she desires, depending upon its intended use. Typically, the user uses 0.7 g to 1 g of powder per application, typically from about one to about five times per day.

The following non-limiting examples illustrate the formulations of the present invention.

| Ingredient | Example IA % W/W | Example IIA % W/W | Example IIIA % W/W | Example IVA % W/W |
|---|---|---|---|---|
| Silica (Microspheres) | — | 10 | — | 15 |
| Silica (Ellipsoids) | 5 | — | 15 | 20 |
| Fumed Silica | — | 1 | 2 | — |
| Magnesium Carbonate | — | 3 | — | — |
| Calcium Silicate | — | 15 | — | — |
| Cornstarch | — | 37.7 | 42.5 | 47.7 |
| Rice Starch | 55.2 | — | — | — |
| Zinc Stearate | — | 3 | — | 10 |
| Magnesium Stearate | 15 | — | 3 | — |
| Nylon | — | 5 | 10 | — |
| Polyethylene | 10 | — | — | — |
| Mica | 10 | 5 | — | — |
| Lauroyl Lysine | — | 7 | 20 | 1 |
| Optional Ingredients* | 4.8 | 13.3 | 7.5 | 6.3 |
| TOTAL | 100 | 100 | 100 | 100 |

*The Optional Ingredients above could comprise ingredients such as odor control agents, skin aids, antimicrobials, antipruritics, perfumes, colorants, or preservatives.

Examples IB–IVB comprise the Examples IA–IVB, respectively, wherein the Optional Ingredients are as follows (by weight of the total body powder).

| Ingredient | Example IB % W/W | Example IIB % W/W | Example IIIB % W/W | Example IVB % W/W |
|---|---|---|---|---|
| Cyclodextrin | — | 3 | 2.9 | — |
| Sodium Bicarbonate | 2 | — | — | — |
| Triclosan | — | 0.2 | 0.1 | — |
| Zinc Phenolsulfonate | — | 3 | 2 | — |
| Dimethicone | 2.5 | 5 | 2.5 | — |
| Aloe Vera | — | 0.1 | — | — |
| Vitamin E | — | 2 | — | 4 |
| Perfume | — | — | — | 0.5 |
| Methyl paraben | 0.2 | — | — | — |
| Propyl paraben | 0.1 | — | — | — |
| Colloidal oatmeal | — | — | — | 1.8 |
| TOTAL OPTIONAL | 4.8 | 13.3 | 7.5 | 6.3 |

Prepare Examples IA–IVA and IB–IVB as follows: create a mixture by mixing all dry ingredients in a commercially available mixer such as a vee-blender, double cone blender, or ribbon blender until the mixture is uniform; reduce the particle size of the mixture using a grinding/pulverizing technique such as hammer milling, impact milling, ball milling, or fluid energy milling; and create a second mixture by adding any liquid phase skin aids and/or perfumes to the mixture, preferably using spray atomization while mixing for a more even dispersion. The second mixture can then undergo a second pulverizing/grinding step, and if desired, an air classifying operation.

Example V: An obese woman has several large abdominal skin folds wherein excess moisture often accumulates causing discomfort. She wishes to reduce the excess moisture. The woman applies the powder of Example IA by sprinkling the composition from a bottle into the palm of her hand and rubbing the composition into the intertriginous regions between her skin folds as well as other occluded skin sites. The woman feels dry and refreshed (and notices less odor). (Alternatively, the woman applies the powder of Example IIA, IIIA, or IVA and notices similar results).

What is claimed is:

1. A highly absorbent body powder comprising:
   a. from about 2% to about 60%, by weight of the body powder, of a moisture absorber selected from the group consisting of silicas, silicates, carbonates, and mixtures thereof; and
   b. a powder carrier comprising:
      i. from about 3% to about 40%, by weight of the body powder, of a component selected from the group consisting of zinc stearate, magnesium stearate, fatty acid derivatives, and mixtures thereof;
      ii. from about 1% to about 40%, by weight of the body powder, of spherical particles which are selected from the group consisting of nylon, polyethylene, polytetrafluoroethylene, and mixtures thereof;
      iii. from about 5% to about 50%, by weight of the body powder, of one or more platelet-shaped particles; and
      iv. from about 25% to about 90%, by weight of the body powder, of one or more starches.

2. The highly absorbent body powder according to claim 1 further comprising odor control agents.

3. The highly absorbent body powder according to claim 1 wherein the moisture absorbers comprise from about 6% to about 50%, by weight of the body powder.

4. The highly absorbent body powder according to claim 1 wherein the powder carrier comprises: from about 0% to about 20%, by weight of the body powder, of magnesium stearate; from about 0% to about 20%, by weight of the body powder, of nylon; from about 0% to about 30%, by weight of the body powder, of lauroyl lysine; and from about 30% to about 60%, by weight of the body powder, of cornstarch.

5. The highly absorbent body powder according to claim 1 further comprising optional ingredients selected from the group consisting of perfume, colorants, skin aids, antipruritics, flow aids, binders, preservatives, antimicrobials, and mixtures thereof.

6. A highly absorbent body powder comprising:
   a. from about 1% to about 40%, by weight of the body powder, of moisture absorbers selected from the group consisting of silica ellipsoids, silica microspheres, and mixtures thereof, and
   b. a powder carrier comprising:
      i. from about 3% to about 40%, by weight of the body powder, of a component selected from the group consisting of zinc stearate, magnesium stearate, fatty acid derivatives, and mixtures thereof;
      ii. from about 1% to about 40%, by weight of the body powder, of spherical particles which are selected from the group consisting of nylon, polyethylene, polytetrafluoroethylene, and mixtures thereof;
      iii. from about 5% to about 50% by weight of the body powder, of one or more platelet-shaped particles; and
      iv. from about 25% to about 90% by weight of the body powder, of one or more starches.

7. The highly absorbent body powder according to claim 6 further comprising odor control agents.

8. The highly absorbent body powder according to claim 6 wherein the moisture absorbers comprise from about 4% to about 25%, by weight of the body powder.

9. The highly absorbent body powder according to claim 6 further comprising optional ingredients selected from the group consisting of perfume, colorants, skin aids, antipruritics, flow aids, binders, preservatives, antimicrobials, and mixtures thereof.

10. A method of reducing excess moisture comprising applying the composition according to claim 1 to skin.

11. A method of reducing excess moisture comprising applying the composition according to claim 6 to skin.

12. A process of making a body powder having good skin feel characteristics comprising the steps of:
    a. making a mixture of powder carrier, optional ingredients, and moisture absorbers by mixing the powder carrier, the optional ingredients, and the highly effective moisture absorbers in a commercially available mixer until uniform; and
    b. creating a reduced size mixture using a commercially available milling technique selected from the group consisting of hammer milling and impact milling; wherein one or more screens have round hole perforations.

* * * * *